United States Patent [19]
Smith, Jr. et al.

[11] Patent Number: 6,084,243
[45] Date of Patent: Jul. 4, 2000

[54] APPARATUS AND METHOD FOR CONTAINING RADIOACTIVE SOURCES

[75] Inventors: George M. Smith, Jr., Sewickley; William T. Gerber, Jr., Pittsburgh, both of Pa.

[73] Assignee: BSI Instruments L.P., Aliquippa, Pa.

[21] Appl. No.: 08/963,286

[22] Filed: Nov. 3, 1997

[51] Int. Cl.$^7$ ........................................... G21F 5/00
[52] U.S. Cl. ........................ 250/506.1; 250/496.1
[58] Field of Search ..................... 250/506.1, 496.1, 250/497.1, 357.1, 356.2, 358.1, 359.1

[56] References Cited

U.S. PATENT DOCUMENTS

| | | | |
|---|---|---|---|
| 3,681,595 | 8/1972 | Dahlin | 250/252.1 R |
| 4,069,423 | 1/1978 | Garrett | 250/493.1 |
| 4,081,688 | 3/1978 | Fries | 250/506.1 |
| 4,362,939 | 12/1982 | Horiuchi et al. | 250/358.1 |
| 5,021,666 | 6/1991 | Reber | 250/359.1 |
| 5,315,124 | 5/1994 | Goss et al. | 250/496.1 |
| 5,564,487 | 10/1996 | Cahill et al. | 164/151.3 |

FOREIGN PATENT DOCUMENTS 2 198 843   11/1987   United Kingdom .

*Primary Examiner*—Kiet T. Nguyen
*Attorney, Agent, or Firm*—Kirkpatrick & Lockhart LLP

[57] ABSTRACT

A radioactive source holder for use in radiation absorption gauging is disclosed. The radiation source holder includes a housing body having a cavity therein through a first surface for receiving a plurality of radioactive sources. The radioactive sources are permanently retained in the housing by epoxy or tape. A shipping container for the radioactive source holders is also provided. The shipping container includes first and second cylindrical members formed from lead which are disposed adjacent to the first surface of the housing body and a second opposite surface. The container bodies are attached to the housing body by a retainer such as bolts. Further, a radioactive source assembly is disclosed which includes a plurality of radioactive source holders along with an end shield which are attached to a mounting plate which may be received on a mounting bracket associated with the radiation absorption gauging system. In each embodiment, the level of radiation in directions other than that of the beam path are less than a predetermined amount.

39 Claims, 6 Drawing Sheets

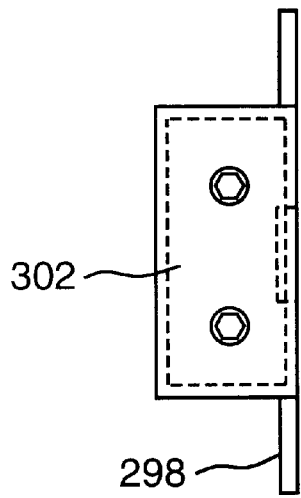
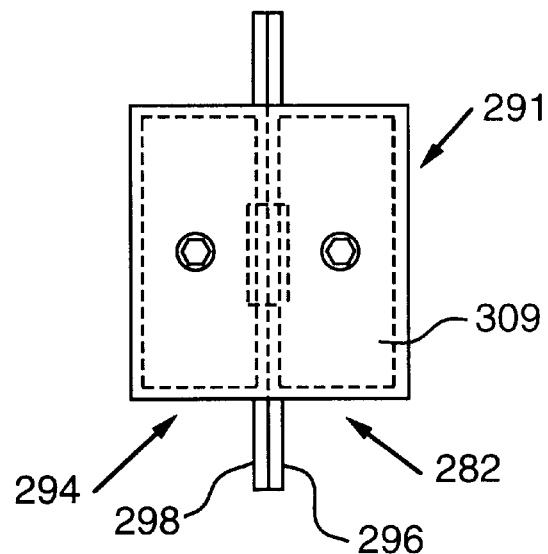
FIG. 11          FIG. 12
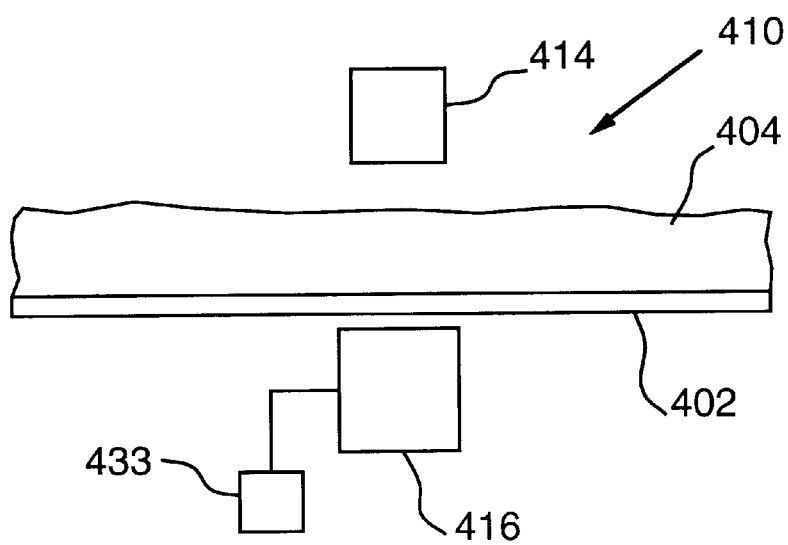
FIG. 8

APPARATUS AND METHOD FOR CONTAINING RADIOACTIVE SOURCES

BACKGROUND OF THE INVENTION

1. Field of the Invention

The subject invention relates to methods and apparatus for containing radioactive sources and, more particularly, to containing low level radioactive sources for shipment and subsequent handling.

2. Description of the Invention Background

In various industrial and commercial operations, there is a need to measure the density or specific gravity of process liquids, suspensions or bulk materials flowing in pipes or contained in tanks or vessels. There is also the need to detect the presence or absence of process material in tanks, pipes, hoppers and chutes, as well as to continuously monitor the level of material therein.

A prior technique of measuring density and/or level within tanks, pipes, hoppers and chutes (collectively referred herein as "conduits") employed a technique known as radiation absorption gauging. Another application of the use of radiation absorption gauging techniques is in measuring the level of molten metal in a continuous casting apparatus as shown in Cahill et al., U.S. Pat. No. 5,564,487, the disclosure of which is hereby incorporated by reference. The radiation absorption gauging technique includes the provision of a radioactive source and a detector spaced therefrom. The radioactive source comprises a material that is continuously disintegrating and which emits particles and energy in the form of alpha, beta and gamma rays in transitioning to a lighter elemental material. The detector is responsive to the impingement of these particles/energy to provide a given signal level which is inversely proportional to the square of the distance between the source and the detector. When an object is disposed between the source and detector, or the aggregate density of medium between the source and detector is otherwise increased, the source emissions will be absorbed by the increased mass of the intervening medium and the output signal from the detector will be proportionately reduced.

This principle may be used to detect the density of material within a conduit by disposing a radioactive source on one side of, or within, the conduit and a detector on the opposite side. As such, the radiation field created by the source passes through the conduit and the material therein before impinging on the detector. By proper calibration techniques, the material passing through the conduit absorbs radiation thereby diminishing the output signal from the detector by a measurable amount.

The same principles are involved in gauging the level of material in a vessel. In this situation, the radioactive source is disposed on one side of a conduit and the detector is disposed on the opposite side of the conduit. There is thus created a radiation field that spans a portion of the height of the conduit. The intensity of the radiation impinging on the detector and the output signal therefrom is inversely proportional to the degree to which the material in the conduit absorbs radiation which, in turn, is a function of the level of the material in the conduit.

In each of the above described measuring techniques, the radioactive source has historically comprised material such as cesium-137 which emits radiation in the range of 0.001 to over 5 curies. Radioactive sources of such intensity are regulated by federal and state regulations throughout the world due to concerns associated with radiation sources of such levels. Such concerns include those associated with the handling of such radioactive sources to insure that workers were not exposed to dangerously high levels of radiation. Similarly, the shipment of such radiation sources in interstate commerce has been heavily regulated to ensure the safe and error free handling of radioactive sources. Further, the disposal of radiation sources of such intensity is regulated to insure that radiation sources do not contaminate landfills, water supplies or other natural resources.

In response to the several concerns relating the use of strongly radioactive sources, the applicant and others have developed technology whereby lower level radioactive sources may be employed. Such sources have radioactive material, such as cesium-137, colbalt-60 or americium-241 in units measured in the micro-curie ($10^{-6}$ curie) range. For example, a cesium-137 radioactive source may be provided in units of less than 10 micro-curies substantially exempt from regulation. By means of comparison, common household smoke detectors may contain americium radioactive sources which contain radioactive sources in the range of 1 micro-curie. Such low level radioactive sources are usually not regulated to nearly the extent as stronger radioactive sources. For present purposes, the regulation of concern is that radioactive sources not be shipped or installed in packages containing more than 100 micro-curies of radioactive material. Further, some of the shipping requirements of low level radioactive sources require that less than a predetermined amount, such as 0.5 milliRem per hour, be emitted at the surface of the container. Indeed, some jurisdictions have imposed standards at the level of 0.1 milliRem per hour. However, even low-level radioactive sources mounted on small disks, spheres, pellets, rods, etc. are shipped loose in containers and require further handling and assembly into the radiation absorption gauging system on site. Heretofore, there has not been a preassembled package of low-level radioactive sources for immediate insertion into a measuring system. Furthermore, there has not been a suitable, reusable shipping container for a plurality of low-level radioactive sources.

Thus, there is a need for a preassembled holder for a plurality of low level radioactive sources. There is also a need for a shipping container for low level radioactive sources which will allow for the safe shipment of such sources without regulation. There is still another need for an assembly of low-level radioactive sources which may be repeatedly used or taken off-line.

The instant invention is directed toward a holder and a container for low level adioactive material which can be used in connection with density, level and/or belt weighing gauge systems for radiation absorption gauging.

SUMMARY OF THE INVENTION

In accordance with a particularly preferred form of the present invention, there is provided a holder for a plurality of radioactive sources. The holder is formed from lead or lead alloy, tungsten alloy or steel alloy or other high density material as a short cylindrical housing body having a central cylindrical cavity therein and opposed planar faces having openings which extend into the cavity. The internal diameter of the cavity is approximately the same size as the disk-shaped diameter of the radioactive sources. Inert end-caps may be provided on opposite ends of a stack of, for example, ten (10) radioactive sources and the resulting stack is inserted into the cavity. Such stack is then permanently retained within the housing by means of mylar or metal tape or epoxy. Radiation will thus pass from the holder in a beam path facing in the direction of the cavity's opening. In this configuration, the level of radiation on the surfaces of the holder normal to the beam path may be maintained below a predetermined amount, such as 0.5 milliRem per hour.

This invention also includes the provision of a shipping container for an assembly of the holder with a stack of radioactive sources retained therein. The shipping container comprises a pair of cylindrical container bodies having approximately the same outside diameter as that of the housing body. The respective container bodies have planar faces which engage the respective faces of the housing body. Bores are provided through the first and second bodies and the housing body in order that attachment bolts may pass therethrough and be retained therein by corresponding nuts. The shipping container will contain the radioactive sources such that the level of radiation on its surface will be less than a predetermined amount, such as 0.5 milliRem per hour.

In operation, the bolts are removed and the holder with the radiation sources previously mounted therein may be readily inserted in to a radiation absorption gauging apparatus. In such apparatus, the holder with the radioactive sources mounted therein is provided on one side of a conduit by mounting the same on a mounting plate. A rear shield which is formed as a cylindrical lead body similar to the first and second container bodies is mounted on the side of the housing opposite the conduit. The detector is mounted on the opposite side of the conduit from the radiation source. A microprocessor unit is coupled to the scintillation detector to calculate the appropriate density or level measurements.

In an alternative embodiment of the invention, the holder for radioactive sources is formed as a two-piece column with a series of recesses therealong. The radioactive sources are mounted in the cavities. For shipment, the pieces of the column form the shipping container. In that case, the pieces of the column are separated and deposed in confronting relationship. End members are provided so that the level of radiation on the surface of the container is less than a predetermined amount, such as 0.5 milliRem per hour.

Accordingly, it is a feature of the present invention to provide a holder assembly for radioactive sources.

It is another feature of the present invention to provide a shipping container for radioactive sources.

It is yet another feature that the radioactive source assembly, or even the system itself, may serve as the shipping container whose surface radiation is less than a predetermined amount.

Accordingly, the present invention provides solutions to the shortcomings of prior radiation absorption gauging systems by providing apreassembled, permanent holder for radioactive sources, a shipping container therefor and a radioactive source assembly for use in such system. Those of ordinary skill in the art will readily appreciate, however, that these and other details, features and advantages will become further apparent as the following detailed description of the preferred embodiments proceeds.

BRIEF DESCRIPTION OF THE DRAWINGS

In the accompanying Figures, there are shown present preferred embodiments of the invention wherein like reference numerals are employed to designate like parts and wherein:

FIG. 8 is a schematic representation of a radiation absorption belt weight/mass gauging system according to the present invention;

FIG. 11 is an end elevation of the source assembly of FIG. 10; and

FIG. 12 is an end view of an end member used for shipping purposes.

DETAILED DESCRIPTION OF THE PREFERRED EMBODIMENTS

Figure 1:
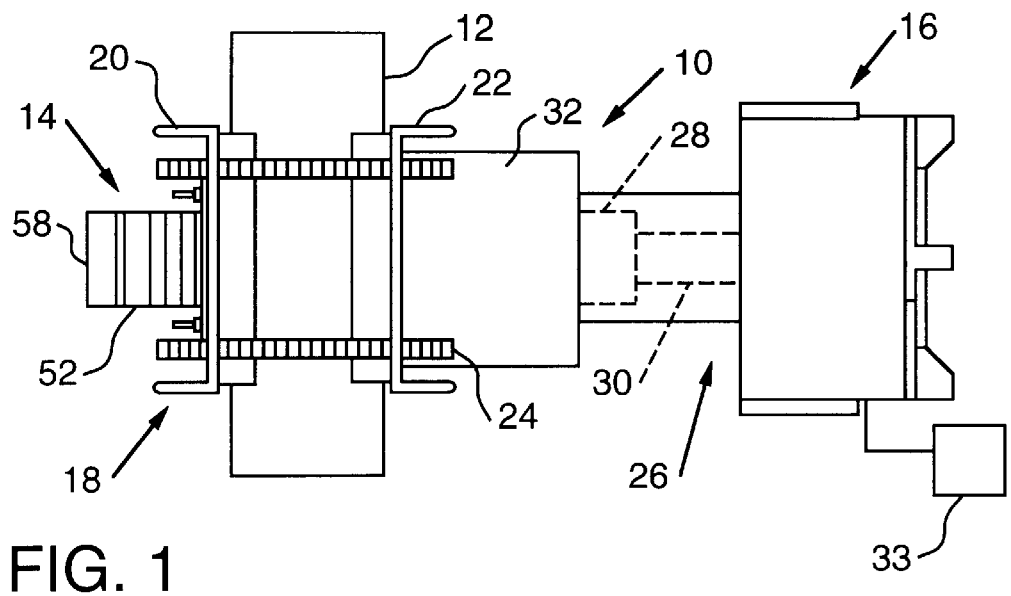
FIG. 1 is a schematic side elevation view of a radiation absorption gauging system according to the present invention.
Figure 2:
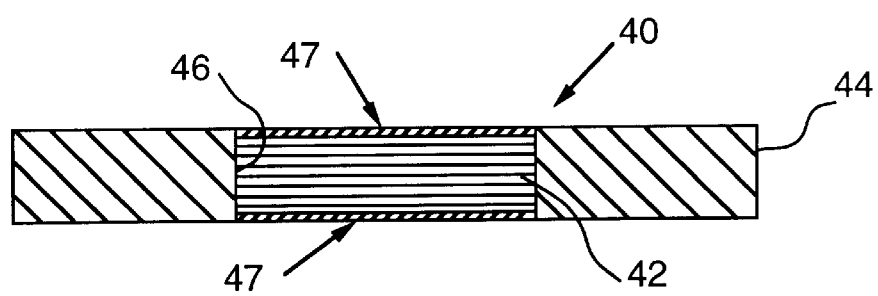
FIG. 2 is a side cross-sectional view of the radiation source holder according to the present invention.

Referring now to the drawings for the purposes of illustrating the present preferred embodiments of the invention only and not for the purposes of limiting the same, the Figures show a radiation absorption gauging system, generally shown as 10, installed on a conduit or vessel 12. The radiation absorption gauging system 10 includes a radioactive source, generally shown as 14, and a detector, generally shown as 16. The radioactive source assembly 14 and the detector 16 are attached on opposite sides of the conduit 12 by means of a mounting assembly generally shown as 18. The mounting assembly 18 includes a first mounting bracket 20 to which the radiation source 14 is attached and a second mounting bracket 22 to which the detector 16 is attached. Threaded rod and bolts 24 connect the first and second mounting brackets 20 and 22, respectively.

The detector 16 includes a scintillation detector 26 which is used to measure the strength of the radiation field after it has passed through the pipe 12 and any process material therein. The strength of the signal is related to the density of the process material. As the density of the process material increases, the strength of the signal decreases. The scintillation detector includes a scintillation crystal, generally shown as 28, and a photomultiplier tube, associated electronics and voltage divider, generally shown as 30. A lead collimator 32 is positioned around the end of the scintillation detector 26. The collimator 32 functions to shield the scintillation detector from stray background radiation which will affect the measurement. A microprocessor amplifier 33 is coupled to the detector 26 to calculate the desired measurement.

In use, the radioactive source 14, such as cesium-137, generates gamma waves. Alternative sources include cobalt-60 or americium-124. The gamma waves exit the radioactive source 14 from the side facing the conduit 12. The gamma waves travel through he conduit 12 where some of it is absorbed by the material therein. The gamma waves strike the scintillation crystal 28 generating a light photon. The detector 16 converts the light photon into digital pulses which are transmitted to the microprocessor 33 which is calibrated to transform the digital pulses into representative units such as density or concentration.

The radiation source 14 includes one of more source holders generally shown as 40 having a plurality of radioactive sources 42 mounted therein. More specifically, the source holder 40 includes a cylindrical housing body 44 formed from a lead alloy, tungsten alloy, a steel alloy, or other high density material (possibly even spent uranium) and having a central cavity or bore 46 passing therethrough. By means of example, the housing body may be approximately 3.5 to 4.5 inches in diameter, 0.24 inches high and the bore 46 may be 0.96 inches in diameter. The radiation sources 42 are, for example, thin disks with less than 10 micro-curies of cesium-137 deposited on 9 milligram per square centimeter of polyamide and covered with a 0.010 inch of aluminized mylar foil. The cesium-137 serves to generate gamma rays for the detection purposes described herein. Alternatively, the sources 42 may be formed as small spheres, pellets, rods, etc. and may be formed from cobalt-60 or americium-241. The diameter of the bore 46 is approximately equal to the outer diameter of the disks on which the radioactive sources 42 are mounted, in such embodiment. Inert filler plugs 47 or tape are provided on the outer ends of the stack of radioactive sources 42. It is important to note that the thickness of the source holder 40 is sufficient to prevent radiation exceeding a predetermined level, such as 0.5 milliRem per hour or 0.1 milliRem per hour in some cases, from being present on the outer radial surface of the source holder 40. Indeed, it is a principal feature of this invention that in each embodiment disclosed, be it of the system 10, radiation source 14, the source holder 40 or the shipping container 60 (described below), and other embodiments thereof, that the level of radiation on any surface other than in the radiation beam path be below a predetermined limit. Typically, such predetermined limit will be that level which may be handled and shipped without significant regulation. Currently, such levels are less than 0.5 milliRem per hour in most situations and less than 0.1 milliRem per hour in some cases.

In accordance with this invention, a plurality of the radioactive sources 42 are permanently preassembled into the source housing body 44. As used herein, "permanently" is intended to indicate that the radioactive sources 42 cannot be removed from the housing body without damaging the sources 42, the holder assembly 40 or the retainer therefor. "Preassembled" is intended to mean that the radioactive sources 42 are permanently fixed in the housing body 44 at a time and place remote from the installation of the radioactive sources into the radiation absorption gauging system 10.

As shown in FIG. 1 one or more radiation source holder assemblies 40 may be mounted on the first mounting bracket 20 by means of a mounting clamp adapter plate 48 as shown in FIG. 1. A front support plate 50 is provided between the source holder 40 and the mounting clamp adapter plate 48. A cylindrical lead end cap 52 is provided on the side of the radiation source 14 remote from the mounting clamp adapter plate 48. By means of example, the end cap 52 may be 1.4 inches in height and 3.5 to 4.5 inches in diameter. A rear support plate 54 is provided adjacent to the end cap 50. One way fasteners, such as screws 56, are provided to clamp the entire assembly including the rear support plate 54, end cap 52, radioactive source holders 40 and the front support plate 50 to the mounting clamp adapter plate 48 so that removal therefrom is difficult. In addition, a lead storage cap 58 may be secured to the end cap 52 by means of screws 60. For example, the storage cap 58 may be 1.4 inches in height and 3.5 to 4.5 inches in diameter. Alternatively, the storage cap 48 may be hingedly attached to the mounting clamp adapter plate 48. In any event, in its storage condition, the assembly must provide surface radiation levels less than, for example, 0.5 milliRem per hour. Also, alternatively, the end cap 54 and the source holders 40 may be formed as a unitary component. Indeed, the entire radiation absorption gauging system 10 may be formed as an assembly when conduit 12 is a flanged conduit that can be inserted into another line, so long as the radiation on any external surface of system 10 is less than a predetermined amount, such as 0.5 milliRem per hour.

Figure 3:
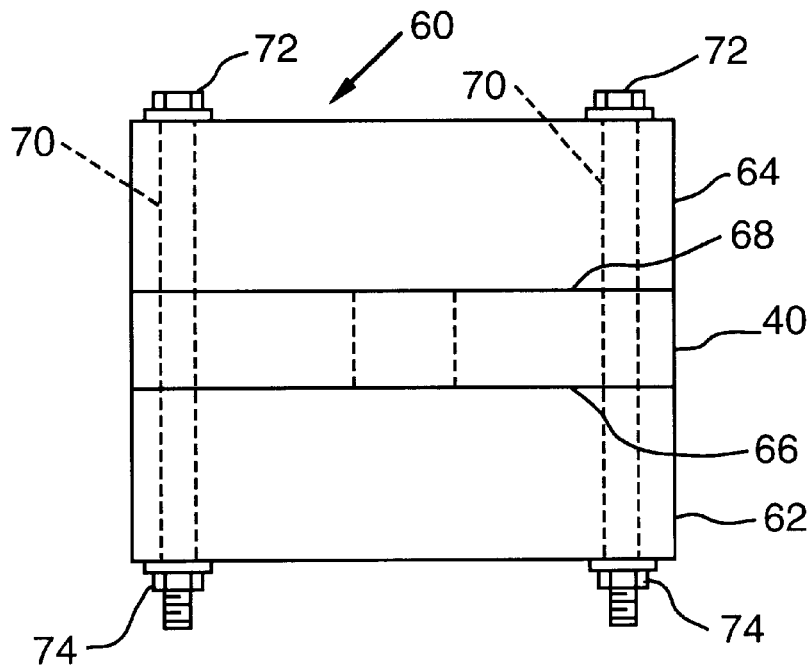
FIG. 3 is a side elevation view of a radiation source shipping container according to the present invention.
Figure 4:
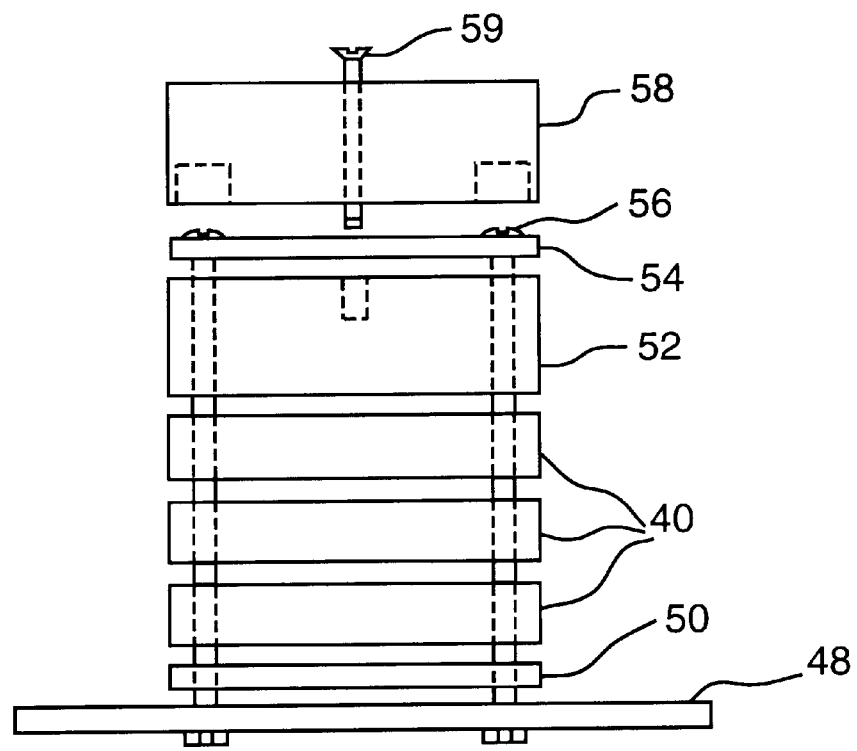
FIG. 4 is an exploded side elevational view of the radiation source assembly according to the present invention.
Figure 5:
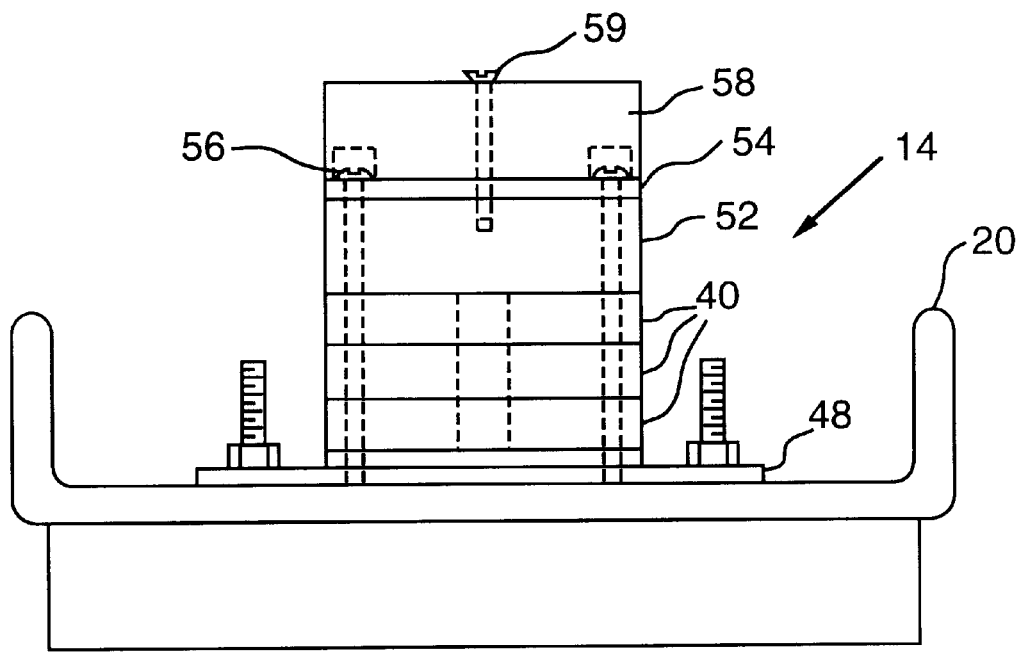
FIG. 5 is a side elevation view of an assembled radiation source assembly according to the present invention.
Figure 6:
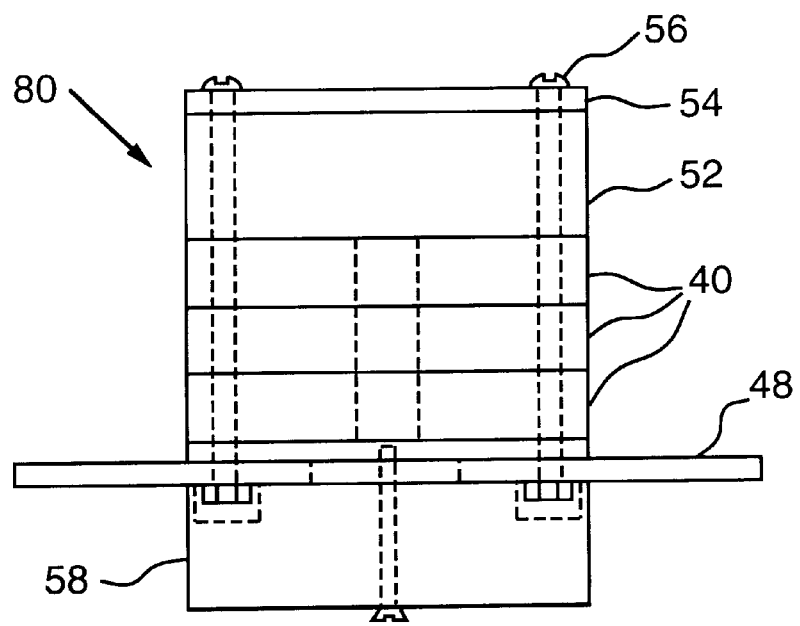
FIG. 6 is a side elevation view of the radiation source assembly according to the present invention in its storage configuration.

In accordance with a present preferred embodiment of the invention, there is shown a shipping container, generally shown as 60, for the source holder 40. As shown in FIG. 3, the shipping container 60 includes a first container body member 62 and a second container body member 64 which, when assembled, are adjacent the first face 66 and second face 68, respectively, of the source holder 40. Preferably, the first and second housing members 62 and 64, respectively, are formed from a lead material or a lead alloy, tungsten alloy, steel alloy or other high density material and are cylindrically shaped so that their outer diameters are approximately the same as the outer diameter of the source holder 40. For example, the first and second body members 62 and 64 may be 1.4 inches in height and 3.5 to 4.5 inches in diameter. However, the housing members may be of alternative shapes, such as square shaped. Bores 70 are provided through the first and second body members 62 and 64, respectively, and through the source holder 40 so that bolts 72 and nuts 74 may join the assembly in forming a shipping container 60 for shipment of the source holder 40. Alternatively, the first body member 62 may be unitary with the source body housing 44. As used herein, "unitary" means that such members may be formed as a single piece or formed as two pieces that are joined with the joint being sufficient to prevent more radiation from passing therethrough than through the walls of the members. The thickness of the first and second housing members 62 and 64 is sufficiently great that at all points on the periphery thereof, the level of radiation is less than 0.5 milliRem per hour. All components of the shipping container 60 are assembled and shipped in a shipping package, such as a tube, box or other package formed from plastic, cardboard or other suitable material. In use, a user receiving the shipping container 60 may remove nuts 74 from bolts 72 and remove the first body member 62 from the source holder 40. The source holder 40 may then be inserted into the radiation source 14 in an assembly 10 and the first body member 62 reassembled onto bolts 72 by means of nuts 74 and the shipping container returned to the manufacturer. By virtue of the provision of the shipping container 60, the source housings 40 will be shipped in commerce in compliance with applicable regulations. It should also be understood by those skilled in the art that the shipping container 60 may also serve as part of the radiation source assembly 14 wherein the second body member 64 acts as the end cap 52. Also, the storage container 80 may also serve as the shipping container 60.

When it is desired to deactivate the system 10, such as for maintenance, the source assembly 14 should be removed from the conduit 12 and placed into a safe condition by forming a storage assembly 80. To accomplish this, the source holder 40 is removed from the first bracket 20. Thereafter, the screw 59 is removed thereby allowing the removal of rear housing 58. Rear housing 58 is then provided on the opposite side of the mounting clamp adapter plate 48 and the screw 59 is used to attach it to the mounting clamp adapter plate 48. As such, the radioactive sources 42 will be surrounded by lead material so that in all directions surrounding the storage assembly 80, the level of radiation is less than, for example, 0.5 milliRem per hour.

Figure 7:
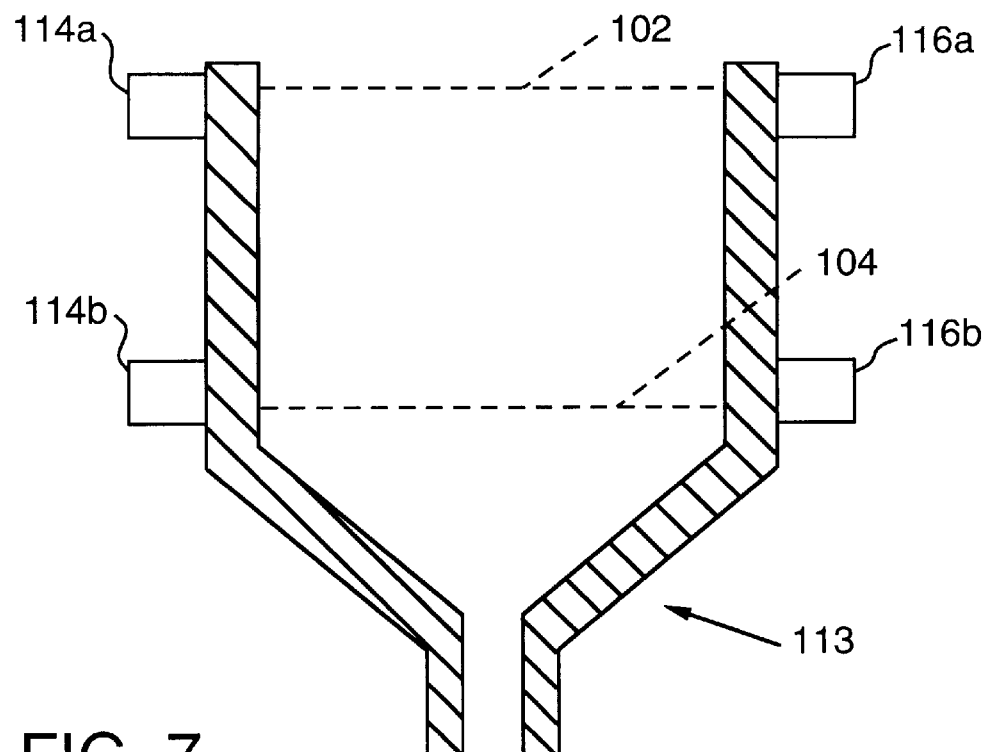
FIG. 7 is a schematic representation of a radiation absorption point level gauging system according to the present invention.

Another embodiment of the invention is shown in FIG. 7 wherein the elements have similar numerals to those described above but increased by the value of 100. In this embodiment, there is shown a radiation absorption gauging system 100 for use in detecting the presence or absence of process material and provides a minimum or maximum level indication for tanks, pipes, hoppers and chutes. The system 100 includes a first radioactive source 114a and a first detector 116a mounted on opposite sides of the tank 113 to indicate a first level 102. There is also provided a second radioactive source 114b and a second detector 116b to indicate a second level 104. It will be appreciated that the construction of detectors 116a and 116b are similar to that of the detector 16 described above. Furthermore, the construction and operation of the radioactive sources assembly 114a and 114b are similar to those described above in respect to radioactive source assembly 14. The operation of system 100, however, merely serves to indicate whether there is material between the respective radiation sources and detectors. As such, if detector 116b detects material and detector 116a detects material, the system may generate an output indicating that a first high level 102 is achieved in the tank 113. However, if detector 116b detects material and detector 116a does not, the system will generate a signal indicating that the level of material in vessel 113 is between the respective high 102 and low 104 levels. If, however, detector 116b does not detect material in vessel 113, a signal will be generated indicating that the level of material is below that of the low level 104. It will, of course, be appreciated by those skilled in the art that if only a single level measurement were desired, only one source/detector combination such as 114a and 116a or 114b and 116b may be employed.

Another embodiment of the invention is shown in FIG. 8 wherein a radiation absorption gauging belt weighing system 410 is disclosed. In the belt weighing system 410, a belt 402 movably supports material to weighed 404 therein. One or more radiation source assembly(s) 414 are provided on one side of the belt 402 and a radiation detector 416 is provided the opposite side with source assemblies 414 either above or below the belt 402. As such, the material 404 passing on the belt 402 absorbs some of the radiation passing from the source 414 to the detector 416. By proper calibration, the weight of the material 404 can be calculated by a microprocessor 433 based on the amount of radiation which is ultimately sensed by the detector 416.

Figure 9:
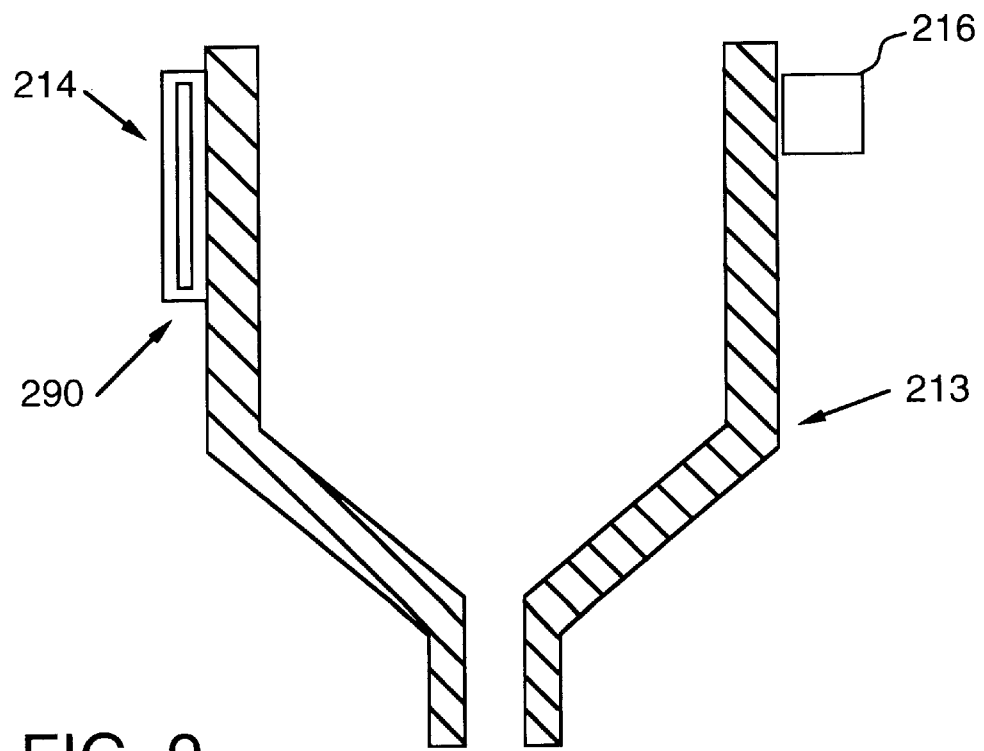
FIG. 9 is a schematic representation of a radiation absorption continuous level gauging system according to the present invention.
Figure 10:
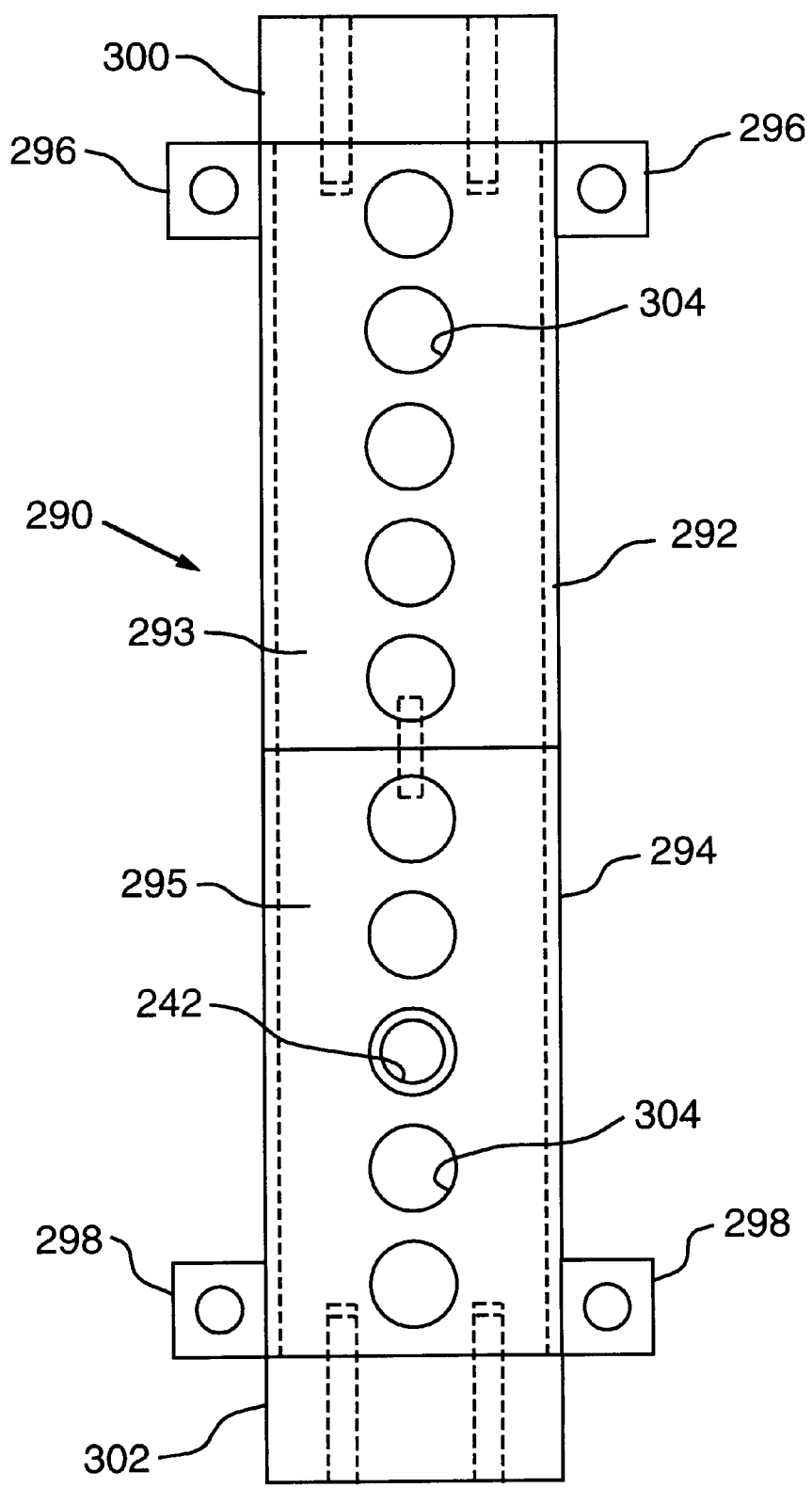
FIG. 10 is a front elevation view of an alternative radiation source assembly according to the present invention.

Yet another embodiment of the invention is shown in FIG. 9. This embodiment provides a continuous level indication of materials in tanks, pipes, hoppers and chutes, such as vessel 213. In this system, a detector 216 is provided similar to detector 16 described above. However, the radioactive source indicated as 214 is instead arranged in a column. That is, the radioactive source 214 includes a plurality of radioactive sources which are mounted in a housing generally shown as 290. The housing 290 is preferably formed from lead, lead alloy, tungsten alloy or steel alloy. The housing 290 is preferably formed as two members 292 and 294, respectively, which may be joined in end-to-end relationship by fasteners such as screws. The housings 292 and 294 may each be, for example, 6.25 inches by 3 inches by 1.5 inches. The housings 292 and 294 have laterally extending flanges 296 and 298, respectively. Additionally, end members 300 and 302 are attached to the members 292 and 294, respectively, by fasteners such as screws. The end members 300 and 302 may be, for example, 3 inches by 1.5 inches by 1.25 inches. The members 292 and 294 have a series of recesses 304 formed therein in a colurn on their faces 293 and 295, respectively. The recesses may either receive a radioactive source 242 which are like the sources 42 therein to generate an elongated radiation field. As such, the housing 290 may be attached to a vessel 308 by fasteners through flanges 296 and 298 to measure the level of material therein. Such measurement is made possible by virtue of the elongated radiation field created by the sources 242 and the detection and calculation capabilities of the detector 216. Again, it will be appreciated that due to the structure of the housing 290, the level of radiation on all surfaces thereof, except in the direction of the radiation beam path normal to the faces 293 and 295, will be at an acceptably low level such as 0.5 milliRem per hour.

The housing 290 may also serve as a shipping container 291 for the radioactive sources 342 mounted therein. In that case, the housings 292 and 294 may be separated and positioned with faces 293 and 295 in confronting relationship. Fasteners then join the flanges 296 and 298 to one another An end protector 309 is provided to cover and join the ends of the housings 292 and 294 remote from end members 300 and 302. The end protector may be 3 inches by 3 inches by 1.5 inches. Again, it is important that, when assembled, the level of radiation on the surface of the shipping container 291 be acceptably low, e.g., 0.5 milliRem per hour.

Thus, from the foregoing discussion, it is apparent that the present many of the problems encountered by prior radiation absorption gauging systems are overcome. Those of ordinary skill in the art will, of course, appreciate that various changes in the details, materials and arrangement of parts which have been herein described and illustrated in order to explain the nature of the invention may be made by the skilled artisan within the principle and scope of the invention as expressed in the appended claims.

What is claimed is:

1. A preassembled radioactive source holder assembly for radiation absorption gauging, comprising:
   a housing body having a cavity open through a first surface of the housing body;
   at least one radioactive source in said cavity; and
   a retainer for permanently retaining said at least one radioactive source in said cavity, wherein the level of radiation on the surfaces of said housing body normal to said first surface is less than about 0.5 milliRem per hour.

2. The assembly of claim 1 wherein said cavity extends through a second surface of said housing body opposite from said first surface.

3. The assembly of claim 1 wherein said housing body is cylindrical.

4. The assembly of claim 1 wherein said housing body comprises lead.

5. The assembly of claim 1 wherein said radioactive source comprises cesium-137.

6. The assembly of claim 1 wherein said radioactive source comprises a plurality of disk-shaped radiation generating members.

7. The assembly of claim 6 wherein said plurality of radiation generating members comprises cesium-137.

8. The assembly of claim 6 further comprising filler plugs disposed in said cavity on the opposite sides of said radioactive source.

9. The assembly of clainm 6 wherein the inner surface of said cavity is of approximately the same size as the outer surface of said radiation generating members.

10. The assembly of claim 1 wherein said retainer comprises epoxy.

11. The assembly of claim 1 wherein said retainer comprises mylar tape.

12. The assembly of claim 1 wherein said retainer comprises metal tape.

13. The assembly of claim 1 further comprising an end housing attached to said housing on the opposite side thereof from said first surface, wherein the radiation level on the surface of said end housing is less than a predetermined amount.

14. The assembly of claim 13 wherein said end housing and said housing body are unitary.

15. The assembly of claim 1 further comprising:
a first container body member adjacent to said first surface;
a second container body member adjacent a second surface of said housing body opposite from said first surface; and
a fastener for attaching the first container body member and the second container body member to said housing body, wherein the radiation level on the surfaces of said first and second container bodies is less than a predetermined amount.

16. The assembly of claim 15 wherein said first and second container bodies comprise lead.

17. The assembly of claim 15 wherein said first container body member and said second container body member are cylindrical.

18. The assembly of claim 17 in which said housing is cylindrical and has a first outer diameter and the outer diameters of said first container body member and said second container body member are substantially the same as the first diameter.

19. The assembly of claim 15 wherein said housing body and said second container body are unitary.

20. A radiation absorption gauging system for gauging material, comprising:
a conduit through which said material may pass;
a preassembled radioactive source holder on one side of said conduit, comprising;
a housing having a cavity open through a first surface of the housing;
at least one radioactive source; and
a retainer for permanently retaining said at least one radioactive source in said cavity;
a detector disposed on the opposite side of the conduit from the radioactive source; and
a support assembly for supporting the radioactive source holder on one side of the conduit and for supporting the detector on the opposite side of the conduit;
wherein the radiation level outside said system is less than about 0.5 milliRem per hour.

21. A shipping container for a radioactive source, comprising:
a housing body having a cavity open through a first surface of the housing body;
a first body member adjacent to said first surface;
a second body member adjacent a second surface of said housing opposite from said first surface; and
a fastener for attaching the first body member and the second body member to said housing;
wherein the radiation level on the outer surface of said housing body and said first and second body member is less than about 0.5 milliRem per hour.

22. The shipping container of claim 21 wherein said housing body and said second container body are unitary.

23. A radioactive source assembly comprising:
at least one preassembled radioactive source holder comprising:
a housing body having a cavity open through a first surface of the housing body;
at least one radiation source; and
a retainer for retaining said at least one radioactive source in said cavity;
an end cap disposed adjacent to a second side of said housing body; and
a joiner for attaching said end cap to said housing body;
wherein, the radiation level on the surface of the end cap and on the surfaces of said housing body normal to said first surface is less than about 0.5 milliRem per hour.

24. The radiation source assembly of claim 23 wherein said housing body and said end cap are unitary.

25. The radioactive source assembly of claim 23 further comprising a first support plate on the opposite side of said end cap from said at least one radiation source holder.

26. The radiation source assembly of claim 25 further comprising a second support plate on the opposite side of said at least one radioactive source holder from said first support plate.

27. The radiation source assembly of claim 26 further comprising an adapter plate on the opposite side of said second support plate from said at least one radioactive source.

28. The radiation source assembly of claim 23 further comprising a cover member which may be disposed in facing relationship to said first surface whereby the radiation level on the outer surfaces of said assembly is less than about 0.5 milliRem per hour.

29. A method of supporting a radioactive source, comprising:
providing a housing body having a cavity for receiving said radioactive source, said cavity being open through a first surface of the housing; and
permanently preassembling said radioactive source into said cavity;
whereby the level of radiation on the surfaces of said housing body normal to said first surface are less than about 0.5 milliRem per hour.

30. The method of claim 29 further comprising:
providing a first container body member adjacent to said first surface;
providing a second container body member adjacent a second surface of said housing body opposite from said first surface; and
providing a fastener for attaching the first container body member and the second container body member to said housing;
whereby the level of radiation on the surfaces of said first and second container bodies is less than a predetermined amount.

31. The method of claim 30 wherein said housing body and said second container body are unitary.

32. A method of preparing a radioactive source for gauging a material, comprising:
providing at least one radioactive source holder comprising:

a housing body having a cavity open through a first surface of the housing body;

a radioactive source; and a retainer for retaining said at least one radioactive source in said cavity;

providing an end cap disposed adjacent to a second side of said housing body; and providing a joiner for attaching said end cap to said housing body;

whereby the level of radiation on the surfaces said end cap and seal housing normal to said first surface are less than about 0.5 milliRem per hour.

33. A preassembled radioactive source holder assembly for radiation absorption gauging, comprising:

a housing body having a cavity open through a first surface of the housing body;

at least one radioactive source in said cavity; and a retainer for permanently retaining said at least one radioactive source in said cavity, wherein the level of radiation on the surfaces of said housing body normal to said first surface is less than about 0.1 milliRem per hour.

34. A radiation absorption gauging system for gauging material, comprising:

a conduit through which said material may pass;

a preassembled radioactive source holder on one side of said conduit, comprising;

a housing having a cavity open through a first surface of the housing;

at least one radioactive source; and a retainer for permanently retaining said at least one radioactive source in said cavity;

a detector disposed on the opposite side of the conduit from the radioactive source; and a support assembly for supporting the radioactive source holder on one side of the conduit and for supporting the detector on the opposite side of the conduit;

wherein the radiation level outside said system is less than about 0.1 milliRem per hour.

35. A shipping container for a radioactive source, comprising:

a housing body having a cavity open through a first surface of the housing body;

a first body member adjacent to said first surface;

a second body member adjacent a second surface of said housing opposite from said first surface; and a fastener for attaching the first body member and the second body member to said housing;

wherein the radiation level on the outer surface of said housing body and said first and second body member is less than about 0.1 milliRem per hour.

36. A radioactive source assembly comprising:

at least one preassembled radioactive source holder comprising:

a housing body having a cavity open through a first surface of the housing body;

at least one radiation source; and a retainer for retaining said at least one radioactive source in said cavity;

an end cap disposed adjacent to a second side of said housing body; and a joiner for attaching said end cap to said housing body;

wherein, the radiation level on the surface of the end cap and on the surfaces of said housing body normal to said first surface is less than about 0.1 milliRem per hour.

37. The radiation source assembly of claim 36 further comprising a cover member which may be disposed in facing relationship to said first surface whereby the radiation level on the outer surfaces of said assembly is less than about 0.1 milliRem per hour.

38. A method of supporting a radioactive source, comprising:

providing a housing body having a cavity for receiving said radioactive source, said cavity being open through a first surface of the housing; and permanently preassembling said radioactive source into said cavity;

whereby the level of radiation on the surfaces of said housing body normal to said first surface are less than about 0.1 milliRem per hour.

39. A method of preparing a radioactive source for gauging a material, comprising:

providing at least one radioactive source holder comprising:

a housing body having a cavity open through a first surface of the housing body;

a radioactive source; and a retainer for retaining said at least one radioactive source in said cavity;

providing an end cap disposed adjacent to a second side of said housing body; and providing ajoiner for attaching said end cap to said housing body;

whereby the level of radiation on the surfaces said end cap and seal housing normal to said first surface are less than about 0.1 milliRem per hour.

* * * * *